United States Patent [19]
Felix et al.

[11] Patent Number: 4,941,872
[45] Date of Patent: Jul. 17, 1990

[54] CONTROL HANDLE FOR SURGICAL IRRIGATION AND SUCTION DEVICE

[75] Inventors: Augustus Felix, Providence; John Uhoch, Warwick, both of R.I.

[73] Assignee: C. R. Bard, Inc., Murray Hill, N.J.

[21] Appl. No.: 693,277

[22] Filed: Jan. 22, 1985

[51] Int. Cl.⁵ .............................................. A61M 1/30
[52] U.S. Cl. ..................................... 604/27; 604/902; 604/39
[58] Field of Search ..................... 604/902, 19, 27, 30, 604/34, 35, 39, 43; 433/80, 88–89, 91, 95, 96, 141, 216

[56] References Cited

U.S. PATENT DOCUMENTS

| | | | |
|---|---|---|---|
| 790,353 | 5/1905 | Estlingen | 604/34 |
| 1,317,851 | 10/1919 | Arnett | 604/34 |
| 2,243,299 | 5/1941 | Travers | 604/39 |
| 2,494,088 | 1/1950 | Dulity | 604/39 |
| 2,531,793 | 11/1950 | Sulek | 604/39 |
| 2,595,491 | 5/1952 | Schweikert | 604/39 |
| 3,771,522 | 11/1973 | Waysilk et al. | 604/39 |
| 4,294,251 | 10/1981 | Greenwald | 604/39 |
| 4,519,385 | 5/1985 | Atkinson et al. | 604/902 |
| 4,526,573 | 7/1985 | Lester et al. | 604/902 |
| 4,553,957 | 11/1985 | Williams et al. | 604/902 |

FOREIGN PATENT DOCUMENTS 1873701 12/1963 Fed. Rep. of Germany ...... 604/902

*Primary Examiner*—C. Fred Rosenbaum
*Assistant Examiner*—Kathleen A. Daley
*Attorney, Agent, or Firm*—Wolf, Greenfield & Sacks

[57] ABSTRACT

A handpiece for a surgical irrigator and suction device includes a drip-free valve arrangement in which the portion of the flexible irrigation conduit is kinked in a V-shape. The handpiece carries a suction wand and an irrigation wand. The wands are easily detachable from the handpiece and can be substituted for wands having other configurations. A retainer clip is provided to prevent inadvertent separation of the wands. The irrigation wand may be used with a debridement nozzle which emits a plurality of distinct irrigation streams in a plane which provides an approved degree of manipulative control for the irrigation procedure.

8 Claims, 2 Drawing Sheets

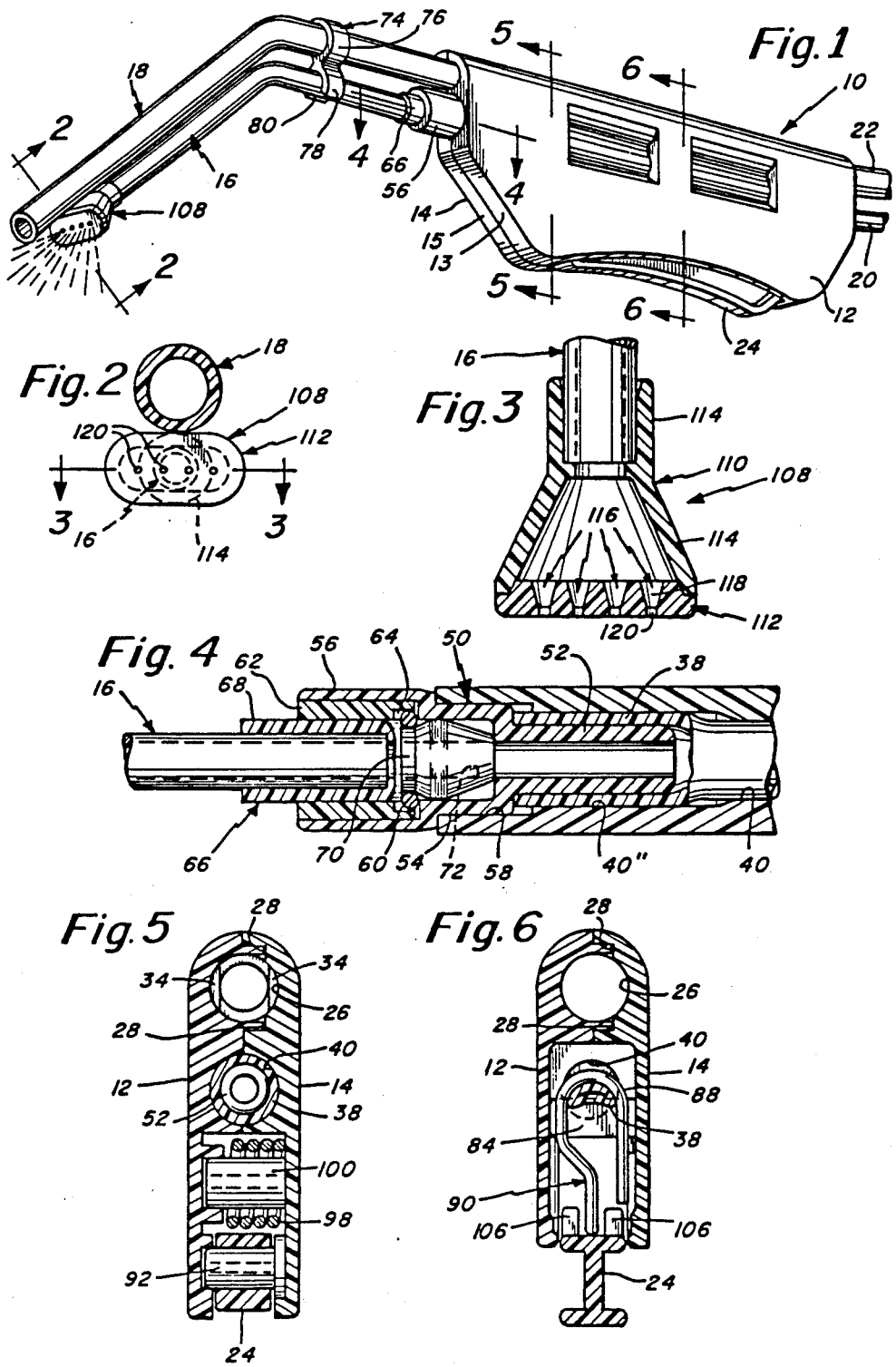

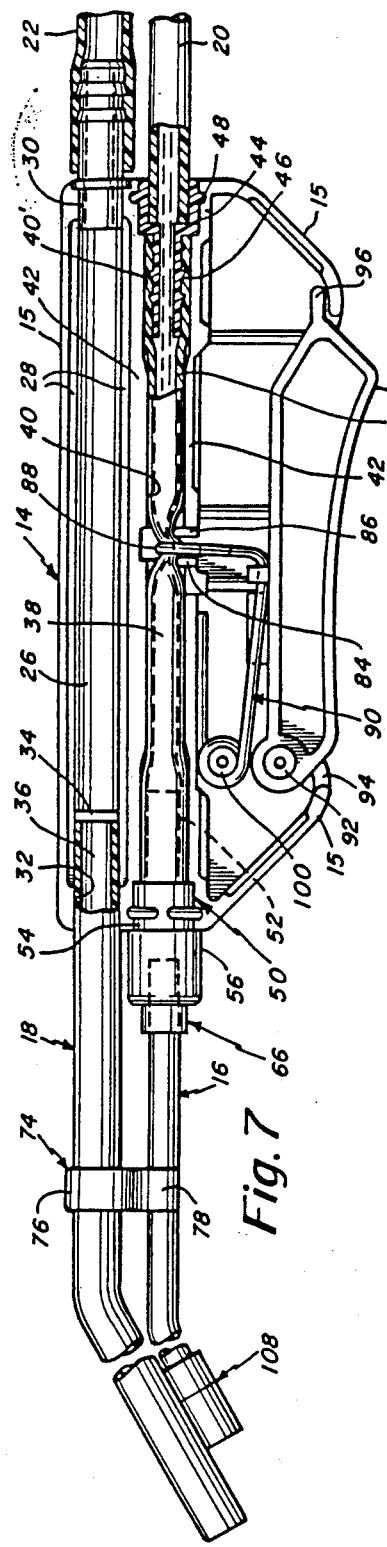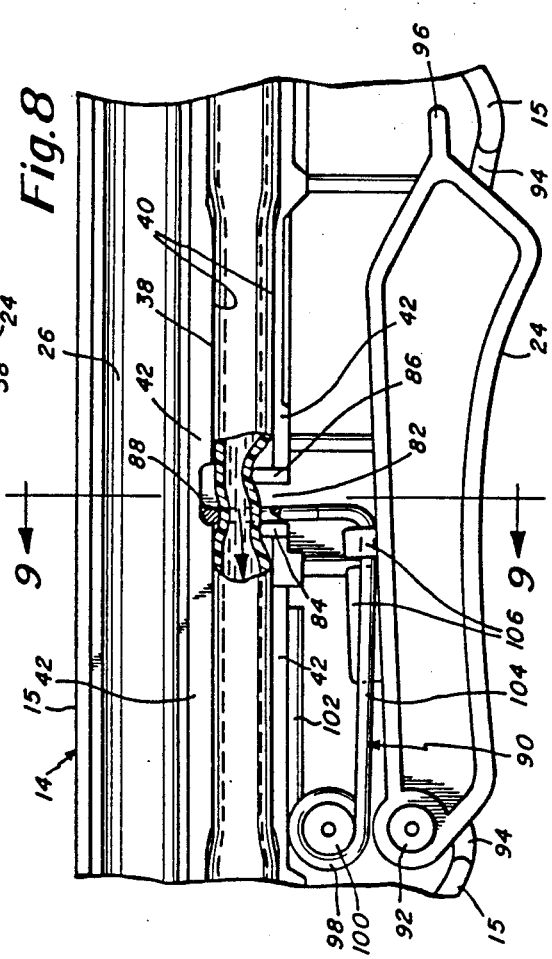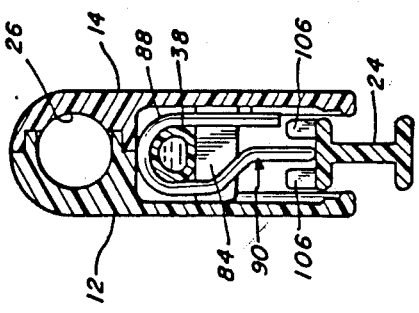

CONTROL HANDLE FOR SURGICAL IRRIGATION AND SUCTION DEVICE

FIELD OF THE INVENTION

This invention concerns a handpiece for a surgical irrigation and suction device for use in irrigation and debridement of a wound or surgical site and suction withdrawal of irrigation and other fluids from the site.

BACKGROUND OF THE INVENTION

It is important during surgical or emergency procedures that the wound or surgical site be maintained clean and antiseptic. Among the common techniques for maintaining a clean surgical site is to irrigate the site with an irrigation or antiseptic solution. Typically the antiseptic solution will be supplied from a reservoir through tubing to a dispensing handle which is manipulated by the surgeon or a surgical assistant. Removal of the irrigation solution as well as other fluids which may collect at the surgical site is removed by applying a suction instrument in the region to withdraw the fluids. The suction instrument may be manipulated by the surgeon or by a surgical assistant Because of the different requirement for different types of surgery there are various styles and sizes of irrigating nozzles and suction devices available For example, surgical procedures which are performed deep within a body cavity, such as deep femoral procedures, require long-tipped instruments with special tips on the end. Other types of procedures require different lengths and shapes for the irrigation and suction instruments.

The present invention relates to an improved handle which is connectable to a source of irrigation fluid as well as a suction source and which has detachable and interchangeable suction and irrigation fittings. The invention also incorporates a trigger and a non-leaking valve mechanism which throttles the outlet for the irrigation fluid to provide a flow control.

SUMMARY OF THE INVENTION

The handle is formed from a pair of mateable plastic sections which house a suction conduit and a irrigation conduit. The proximal end of the handle includes means to connect tubes from a suction source and irrigation fluid source, respectively, to the suction and irrigation conduits within the handle. The distal end of the handle is provide with sockets to receive, detachably, a suction wand and an irrigation wand. The suction and irrigation wands may be interchanged and replaced with other wands of different lengths and/or shapes. A retainer clip is provided to stabilize the wands.

The irrigation wand may be provided with special nozzle arranged to direct a plurality of streams of irrigation fluid in a single plane spray pattern which provides a high degree of controllable cleansing action. The individual streams emitted from the orifices of the nozzle maintain their separation over a substantial distance from the nozzle.

A trigger operated valving mechanism is incorporated into the handle in a manner which provides a leak-proof, drip-free, controlled release for the irrigation fluid. The valving mechanism includes a flexible tube which defines a portion of the irrigation conduit. The valving mechanism includes an arrangement in which the flexible tube is drawn into a V-shaped kinked configuration which fully and completely closes off all flow through the tube and in a manner which avoids leaking or dripping. The spring is connected to a trigger which, when squeezed, shifts position of the spring to release the kink and permit liquid flow. The degree to which the trigger is squeezed controls the degree to which the irrigation flow channel is throttled.

It is among the objects of the invention to provide an improved arrangement for a hand held surgical irrigation and suction device.

Another object of the invention is to provide surgical irrigation handpiece with an improved valving and trigger mechanism to provide controlled release of irrigation fluid.

Another object of the invention is to provide surgical irrigation device which will not drip or leak when released.

A further object of the invention is to provide surgical irrigation and suction handle device with quick detachable suction and irrigation wands to facilitate interchanging of various wand configurations.

Another object of the invention is to provide a device of the type described which is reliable yet is of simple and inexpensive construction and lends itself to one time, disposable use.

Another object of the invention is to provide a surgical irrigation device having a nozzle which emits a plurality of distinct streams of irrigation fluid in a flat planar array to provide a highly controllable degree of cleansing and debridement action.

DESCRIPTION OF THE DRAWINGS

The foregoing and other objects and advantages of the invention will be appreciated more fully from the following further description thereof, with reference to the accompanying drawings wherein:

FIG. 1 is an illustration of the control handle with suction and irrigation wands attached;

FIG. 2 is an illustration of the distal ends of the suction and irrigation tips as seen along the line 2—2 of FIG. 1;

FIG. 3 is a sectional illustration of an improved irrigation nozzle as seen along the line 3—3 of FIG. 2;

FIG. 4 is a sectional illustration of the detachable connection between the irrigation wand and the handle as seen along the line 4—4 of FIG. 1;

FIG. 5 is a sectional illustration of the handle as seen along the line 5—5 of FIG. 1;

FIG. 6 is a sectional view of the handle seen along the line 6—6 of FIG. 1 and illustrating the manner in which the flexible irrigation tube is kinked shut by the valving device;

FIG. 7 is a side elevation of the device with one side of the handle removed and with internal portions shown partly in section;

FIG. 8 is an enlarged illustration similar to FIG. 7 showing the trigger mechanism and valving arrangement with the valve open to permit irrigation fluid to flow; and FIG. 9 is sectional illustration of the handle and valve mechanism as seen along the line 9—9 of FIG. 8.

DESCRIPTION OF THE PREFERRED EMBODIMENT

As shown in FIG. 1 the handle 10 may be formed from a pair of molded plastic side panels which may be referred to, for convenience of description, as a left side panel 12 and a right side panel 14. The side panels 12, 14 are molded with a plurality of internal ribs, grooves and other supporting members which receive the various internal parts of the device and sandwich the various internal parts together when the panels 12, 14 are secured together. The side panels 12, 14 are provided with peripheral walls 13, 15 which meet edge-to-edge when the panels 12, 14 are brought together. The meeting edges of the peripheral walls 13, 15 are secured together as by adhesive, ultrasonic welding or the like. A suction wand 18 and an irrigation wand 16 are detachably connectable to and extend forwardly from the front (distal) end of the handle 10. The rear (proximal) end of the handle 10 is connectable to an irrigation fluid tube 20 which is connectable to a source of irrigation fluid and a suction tube 22 which is connectable to a source of suction. Passageways are formed internally through the handle 10 to communicate irrigation fluid inlet tube 22 with the irrigation wand 16 and the suction tube 22 with the suction wand 18 respectively. The device also includes a trigger 24 which normally projects downwardly through an opening in the bottom of the handle 10. The trigger 24 operates a valve and throttling mechanism within the handle to open and close the irrigation fluid passageway and to throttle and variably control the rate of fluid flow.

The internal arrangement of the panels 12, 14 is illustrated in FIGS. 5-9. As shown in FIGS. 5 and 7 the right side panel 14 is formed to include a longitudinally extending one-half section of a suction passage 26. The left side panel 12 has a similar longitudinally extending half section which, when the panels 12, 14 are mated will define and complete the suction passage 26, as illustrated in FIG. 5. The side panels 12, 14 preferably are provided with mating shouldered surfaces 28 to provide a secure interlocking fit between the panels 12, 14. A fitting 30 is securely attached, as by adhesive, to the rear of the handle and is in communication with the suction passage 26. The fitting 30 is adapted to receive and be attached to the flexible suction tube 22 which, in turn, is connected to a source of suction. The suction wand 18 is detachably connected to the front end of the handle 10 by a socket 32 which is defined at the front end of the suction passage 26. An abutment 34 is formed within each side panel to provide a limit for insertion of the proximal end of the suction wand 18 into the socket 32. The abutments 34 do not obstruct the central passage 36 in the suction wand 18 but merely engage the proximal end of the wall of the suction wand 18. The diameter of the socket 32 is formed so that it can receive the proximal end of the suction wand in a snug but detachable friction fit.

The irrigation conduit is defined by a flexible plastic tube 38 which is confined within a longitudinally extending channel 40. The channel 40 is defined by longitudinally extending ribs 42 which, when the panels 12, 14 are mated, cooperate to define the channel 40. The tube 38 preferably is formed from a material having relatively high elastic memory and may be formed, for example, from silicone rubber. The channel 40 serves the additional purpose of preventing the plastic tube 38 from expanding beyond the confines of the channel 40. This is particularly desirable when the device is to be used with a pulsating irrigation fluid delivery system. The tube 38 is secured at its rear end by a compression fitting 44 which includes a stem 46 which is received within the rear end of the tube 38. The rear portion 40' of the channel 40 is slightly enlarged and is dimensioned with respect to the diameters of the stem 46 and the tubing 38 so that when the panels 12 14 are assembled the rear end of the tube 38 and the stem 46 of compression fitting 44 will be compressed together. The compression fitting assures a proper seal between the plastic tube 38 and the compression fitting 44. The stem 46 also may be provided with one or more barbed rings to engage the inner surface of the tube 38. The compression fitting 44 is further secured between the panels by a circular flange 48 which surrounds the rear portion of the fitting 44 and is received in a circular groove formed along the inner surface of the panels 12, 14. The rear portion of the compression fitting 44 is receptive to the irrigation fluid supply tube 20.

The front end of the flexible tube 38 is secured to the side panels 12, 14 in a similar manner by compression fitting 50 which has a stem 52 received within the front end of the tube 38. The front portion 40" of the channel 40 is formed with a slightly enlarged diameter to receive the combined stem 52 and tube 38 so as to compress them when the panels 12, 14 are secured together.

The compression fitting 50 is provided with an integral socket portion 56 which extends forwardly from the body of the panels 12, 14 and is adapted to detachably receive the proximal end of the irrigation wand 16. The compression fitting 50 has an enlarged portion 54 forwardly of the stem 52. The enlarged portion 54 is received within an enlarged bore 58 formed at the front end of the panels 12, 14. The socket portion 56 extends forwardly from the enlarged portion 54 of the compression fitting 50. The socket portion 56 is arranged to receive the rear end of the irrigation wand 16 in a manner which forms a secure liquid seal yet which permits easy attachment and detachment of the wand 16. On 0-ring 60 is captured within the socket portion 56 to engage the rear end of the wand 16 which is inserted into the socket portion 56. The 0-ring 60 is contained within the socket portion 56 by a sleeve 62 which nests in the internal diameter of the socket portion 56. The inner end of the sleeve 62 is provided with an annular shoulder which defines an annular groove receptive to the 0-ring 60. The inner diameter of the sleeve 62 and the enlarged portion 54 of the compression fitting 50 are substantially the same. The inner diameter of the 0-ring 60 is slightly less so that the 0-ring 60 projects somewhat into the bore defined by the inner diameters of the sleeve 62 and enlarged portion 54.

The rear end of the irrigation wand 16 is provided with a connector fitting 66 which is receivable within the bore of the sleeve 62 and enlarged portion 54 of the compression fitting 50. The connector fitting 66 includes a forward tubular portion 68 which receives and is bonded to the irrigation wand 16. An annular groove 70 is formed above the connector fitting 66 at a location which will receive the 0-ring 60 when the connector fitting 66 is seated fully in the bore of the socket portion 56 and enlarged portion 54. The rearwardmost end of the connector fitting 66 may be tapered rearwardly as shown in FIG. 4. An axial passage 72 is formed through the rearward portion of the connector fitting 66 to maintain communication between the passage and the irrigation wand 16 and the stem 52. From the foregoing it will be appreciated that when the wand 16 with connector fitting 66 is inserted into the socket 56 the 0-ring 60 will effect a seal against the annular groove 70 on the fitting 66 and will also serve to retain the fitting 66 within the socket 56. The wand, with fitting 66 attached, is easily connected and disconnected from a handle yet will maintain a seal when it is connected.

Various shapes and sizes of irrigation and/or suction wands 16, 18 may be employed for use with a variety of surgical conditions as well as surgical preferences. FIG. 1 illustrates but one type of arrangement in which the front end of the wands are bent downwardly at an angle. In that embodiment, as well as in most configurations in which the suction wand 18 will be used, the suction wand will extend somewhat forwardly of the nozzle end of the irrigation wand 16 so that the tip of the irrigation wand 16 will not interfere with the suction operation, particularly when suctioning liquid from cavities or spaces.

The irrigation and suction wands 16, 18 usually will be used together and will be so connected to the handle 10. In order to maintain the wands 16, 18 together and to stiffen the assembly of the wands 16, 18 a retainer clip 74 is provided to secure the wands 16, 18 together. The clip 74 is formed from plastic material having an upper circular collar 76 and an integral pair of downwardly extending arcurate fingers 78. The circular collar 76 mounts on the suction wand 18 and the fingers 78 extend downwardly to define a receptive clip for the irrigation wand 16. The fingers 78 are open at the bottom as indicated at 80. The opening 80 is narrower than the diameter of the irrigation wand 16 to the detachably connectable to the irrigation wand in a snap fit. The snap-fit, detachable retained clip 74 permits either of the irrigation wand 16 or suction wand 18 to be detached independently of the other wand should that be desired.

Flow of irrigation fluid normally is shut off by an arrangement which forms a V-shaped kink in the flexible tube 38. Kinking of the tube is controllably released by squeezing the trigger 24 of the device. As shown in FIGS. 6–9 an intermediate portion of the tube 38 passes over an aperture 82 formed in the lower of the ribs 42 which define the channel containing the flexible tube 38. The aperture 82 is defined by a pair of longitudinally spaced, transversely extending ribs 84, 86. As shown in FIGS. 6 and 7 the portion of the tube 38 which spans t e opening 82 is drawn shut by a hook 88 which partially circles the tube 38 between the ribs 84, 86. The hook 88 is biased downwardly to draw the spanning segment of the tube 38 downwardly and partly into the aperture 82 thus partially wrapping the tube 38 about the ribs 84, 86.. That draws the tube 38 firmly against the upper edges of the ribs 84, 86 to pinch the tube at both of those locations. It also causes a third pinching of the tube 38 by the hook 88 at a location between the ribs 84, 86. Although the device will perform satisfactorily under most conditions when the ribs 84, 86 are approximately the same height, we have found that a more effective seal results when the more upstream of the ribs, here rib 86 has an upper edge which is above the upper edge of the more downstream rib 84. We have found that an arrangement in which the upper edge of the upstream rib is disclosed higher than the upper edge of the downstream rib results in a sharper wrapping of the tube about the upstream rib 86 and provides a more effective seal, particularly when the device is used with higher pressures, on the order of 30 psi and above. The foregoing arrangement results in a drip-proof, leak-proof valve which can be placed confidently on and above the surgical drapes without concern that the device may leak.

The hook 88 preferably is formed integrally with a spring 90 which is arranged to bias the hook 88 in a downward direction, to bias the tube 38 shut. The spring 90 also serves to provide a spring resistance for the trigger 24. The trigger 24 extends generally longitudinally of the housing 10. The trigger 24 is pivoted, at its forward end, to a pivot post 92 formed integrally with and extending from one of the panels, such as the right panel 14. The peripheral walls 13, 15 of the panels 12, 14 are cut away along the lower portion to define a slot 94 through which the trigger 24 projects. The spring 90 is arranged to bias the trigger in a direction which extends out of the slot 94. The rear end cf the trigger has an integrally formed stop member 96 which engages the peripheral wall just rearwardly of the slot 94 to limit and define the maximum extent to which the trigger 24 projects out of the slot 94.

The spring 90 has a wound portion 98 which is mounted about a transversely extending spring support post 100. The spring includes a tail portion 102 which extends from the coiled portion 98 and is captured by engagement with the underside of the lower of the ribs 42 which define the channel for receiving tube 38. The spring 90 also includes a rearwardly extending trigger portion 104 which extends from the other end of the spring coil 100. The trigger portion 104 bears against the upper surface of the trigger 24, rearwardly of the pivot 92 to bias the trigger 24 downwardly. The upper surface of the trigger 24 preferably is provided with a pair of spring guide tabs 106 which embrace the trigger spring portion 104 and maintain it in engagement with the upper surface of the trigger 24.

The hook portion 88 is formed integrally with the spring as an extension from the end of the trigger spring portion 104. The trigger spring portion 104 terminates below the spaced ribs 84, 86 and the hook portion 88 extends upwardly through the aperture 82 to wrap about and engage the tube 38 Thus, the spring 90 serves to draw the tube in a v-shaped, kinked and closed configuration while simultaneously biasing the trigger 24 toward its normal position. As shown in FIG. 8 when the trigger 24 is squeezed the hook 88 is raised to release the kinking effect on the tube 38 and to permit flow of liquid through the tube. The degree to which the trigger is depressed controls the extent to which the tube 38 is opened to flow.

Another aspect of the invention relates to an improved nozzle arrangement for the irrigation wand. The nozzle is arranged to emit the irrigation fluid in a spray pattern which first forms a plurality of coherent separate streams of fluid which remain distinct and in a single plane for a moderate distance. The spray pattern provides for a more controllable cleansing action as compared with conventional circularly arranged stream patterns commonly used in surgical irrigation devices.

As shown in FIGS. 2 and 3, the nozzle, indicated generally at 108, includes a body 110 and an end plate 112. The body has a socket 114 which detachably receives the distal end of the irrigation wand 16. The more forward portion of the body 10 is fan-shaped and flares out, the end plate 112 being bonded to the end of the fan-shaped portion 114. The end plate 112 is provided with a plurality of apertures arranged in a straight line so that the streams will be emitted in a plane. The apertures 116 are formed so that their upstream portions 118 are of larger diameter (they may be tapered as shown) and their downstream portions 120 are cylindrical. The upstream tapered portions 118 extend over the major proportion of the axial length of the aperture 116. The foregoing nozzle arrangement has been found to provide a plurality of coherent streams from the apertures 116 which remains separate for a moderate distance, for example, about one foot. The planar configuration enables the streams to be directed controllably into specific portions of the surgical field with a greater degree of control than prior irrigation nozzles.

It should be understood that the foregoing description of the invention is intended merely to be illustrative thereof and that other embodiments and modifications may be apparent to those skilled in the art without departing from its spirit.

Having thus described the invention what we desire to claim and secure by letters patent is:

1. A handpiece for a surgical irrigator comprising:
   a handle body;
   a flexible fluid conduit extending through the body;
   connector means carried by the handpiece for connecting to the flexible conduit to a source of irrigation fluid;
   means for connecting the other end of the flexible fluid conduit to a fluid outlet;
   means for urging a portion of the flexible conduit transversely to form a V-shaped kink in the conduit to shut off flow through the conduit, said urging means comprising a pair of ribs mounted to the body, the ribs being spaced longitudinally along the flexible conduit, and a member engagable with the conduit at a location between the ribs, said member being constructed and arranged as to draw the conduit transversely between the ribs into said V-shaped kinked configuration and in a manner in which the conduit is wrapped partly about the ribs;
   said ribs being arranged in relative upstream and downstream positions, the more upstream of the ribs having an upper, conduit-engaging edge which is higher than the upper edge of the downstream rib, said height being measured in a direction opposite the transverse direction in which the member is arranged to draw the tube into the V-shaped kinked configuration; and
   means for biasing the member in a direction which shuts off flow through the conduit.

2. A handpiece as defined in claim 1 further comprising;
   a trigger mounted to the body and being constructed and arranged as to overcome the bias means to enable release of the means urging the conduit to the V-shaped kinked configuration.

3. A handpiece as defined in claim 2 further comprising:
   said member and said bias means comprising a spring having a hook portion which engages the flexible conduit between the ribs;
   said spring being contained and mounted within the handpiece so as to bear against the trigger to provide spring resistance against operation of the trigger;
   said hook portion of the spring being arranged to draw the flexible conduit to the V-shaped kinked configuration upon release of the trigger.

4. A handpiece for a surgical irrigation as defined in claim 1 further comprising;
   a fitting mounted to the body at the distal end of the flexible conduit for receiving the inlet end of a suction wand, said fitting and suction wand being constructed and arranged to enable quick, snap-fit detachment of the wand, the fitting having means for effecting a fluid seal to the wand when the wand is attached to the fitting.

5. A handpiece as defined in claim 4 further comprising;
   said fitting comprising a socket having an internal bore and an O-ring retained within the socket, the inner diameter of the O-ring being smaller than the inner diameter of the socket;
   the wand having a connector tip adapted to be received within the socket of the fitting, the connector tip having a peripheral groove adapted to receive and engage the O-ring to effect a fluid seal.

6. A handpiece for a pulsatile surgical irrigator for throttling the pulsatile outlet of the irrigator comprising:
   a handle body having a channel formed internally thereof to contain to contain a flexible conduit;
   a flexible fluid conduit extending through the body and being contained within the channel;
   connector means carried by the handpiece for connecting the flexible conduit to a pulsatile source of irrigation fluid;
   means for connecting the other end of the flexible fluid conduit to a fluid outlet;
   the channel having an aperture to expose a part of the conduit;
   means for urging the exposed part of the conduit transversely to form a V-shaped kink in the conduit comprising hook means moveably mounted to the body and extending into the aperture, the hooks being wrapped about the conduit, the hooks being moveable to urge the exposed part of the conduit to form said V-shaped kinks;
   said channel closely confining the conduit to substantially prevent expansion of the conduit under the influence of positive pressure pulses of said pulsatile flow;
   said flexible fluid conduit is secured within the handpiece body by means comprising;
   a compression fitting connected to each end of the flexible conduit, each of the compression fittings including a rigid stem secured into the opening at each end of the flexible tube;
   said body being formed from a pair of mateable side panels which, when mated, compress the ends of the flexible tube against the stem of the compression fitting.

7. A handpiece for a surgical irrigator and suction device comprising;
   a body;
   a first fluid conduit extending through the body for communicating irrigation fluid from a source thereof to an outlet;
   valve means mounted to the body for controlling fluid flow through the first conduit;
   said fluid conduit terminating in a coupling means for detachable connection to an irrigation wand;
   a irrigation wand detachably connectable to the coupling device;
   a second conduit extending through the body and being connectable to a suction source;
   coupling means at the distal end of the second conduit for detachable connection to a suction wand;
   a suction wand connected to the coupling means at the second conduit;
   a retaining clip attached to the suction wand and irrigation wand for preventing inadvertent separation of the wands;
   wherein said retaining clip comprises;
   a circular ring surrounding the suction wand and being secured thereto, the clip having a pair of projecting fingers arranged arcuately to receive the irrigation wand in a snap fit detachable connection;

said wands being detachable as a unit from the body and said retaining clip being constructed and arranged as to enable the wands to be detached from each other.

8. A handpiece for a surgical irrigator and suction device comprising;

a body;

a first fluid conduit extending through the body for communicating irrigation fluid from a source thereof to an outlet;

valve means mounted to the body for controlling fluid flow through the first conduit;

said fluid conduit terminating in a coupling means for detachable connection to an irrigation wand;

an irrigation wand detachably connectable to the coupling device;

a second conduit extending through the body and being connectable to a suction source;

coupling means at the distal end of the second conduit for detachable connection to a suction wand;

a suction wand connected to the coupling means at the second conduit;

a retaining clip attached to the suction wand and irrigation wand for preventing inadvertent separation of the wands;

a nozzle body attachable to the end of the irrigation wand;

the nozzle having an orifice plate at its distal end;

a plurality of orifices formed in the orifice plate along a straight line, each of the orifices having an enlarged bore at its upstream portion and a narrow diameter bore at its downstream emitting end, the downstream bore being shorter than the upstream portion of the orifice;

said wands being detachable as a unit from the body and said retaining clip being constructed and arranged as to enable the wands to be detached from each other.

* * * * *